United States Patent
Lee et al.

(10) Patent No.: US 10,548,916 B2
(45) Date of Patent: Feb. 4, 2020

(54) COMPOSITION COMPRISING NEOAGAROOLIGOSACCHARIDE AS ACTIVE INGREDIENT, FOR PREVENTION OR TREATMENT OF SEPSIS OR SEPTIC SHOCK

(71) Applicant: DYNEBIO INC., Gyeonggi-do (KR)

(72) Inventors: Je Hyeon Lee, Gyeonggi-do (KR);
Moon Hee Lee, Gyeonggi-do (KR);
Sun Joo Hong, Gyeonggi-do (KR);
Soon Kwang Hong, Seoul (KR)

(73) Assignee: DYNEBIO INC., Gyeonggi-Do (KR)

( * ) Notice: Subject to any disclaimer, the term of this patent is extended or adjusted under 35 U.S.C. 154(b) by 0 days.

(21) Appl. No.: 16/383,311

(22) Filed: Apr. 12, 2019

(65) Prior Publication Data
US 2019/0290678 A1 Sep. 26, 2019

Related U.S. Application Data

(62) Division of application No. 15/541,231, filed as application No. PCT/KR2015/009485 on Sep. 9, 2015, now abandoned.

(30) Foreign Application Priority Data

Dec. 30, 2014 (KR) ........................ 10-2014-0194174

(51) Int. Cl.
| | |
|---|---|
| *C12P 7/40* | (2006.01) |
| *A61K 31/729* | (2006.01) |
| *A23L 29/30* | (2016.01) |
| *A23L 33/125* | (2016.01) |
| *C12P 19/00* | (2006.01) |
| *C12P 19/04* | (2006.01) |
| *C12P 19/12* | (2006.01) |
| *C12P 19/14* | (2006.01) |
| *A23L 33/10* | (2016.01) |
| *A61K 31/702* | (2006.01) |

(52) U.S. Cl.
CPC ............ *A61K 31/729* (2013.01); *A23L 29/30* (2016.08); *A23L 33/10* (2016.08); *A23L 33/125* (2016.08); *A61K 31/702* (2013.01); *C12P 19/00* (2013.01); *C12P 19/04* (2013.01); *C12P 19/12* (2013.01); *C12P 19/14* (2013.01); *C12Y 207/01107* (2013.01); *A23V 2002/00* (2013.01); *A23V 2250/28* (2013.01)

(58) Field of Classification Search
CPC .............................. A61K 31/729; C12P 19/12
USPC ......................................................... 435/183
See application file for complete search history.

(56) References Cited

U.S. PATENT DOCUMENTS

| | | | | |
|---|---|---|---|---|
| 5,418,156 A | * | 5/1995 | Stosz ............. | C12Y 302/01081 435/195 |
| 2005/0020526 A1 | | 1/2005 | Chen et al. | |
| 2012/0220658 A1 | | 8/2012 | Yin et al. | |

FOREIGN PATENT DOCUMENTS

| | | |
|---|---|---|
| KR | 102010014071 | 11/2012 |
| KR | 102013013707 | 6/2016 |

OTHER PUBLICATIONS

Jang, et al., Secretory Overexpression of β-Agarase in Bacillus subtitils and Antibacterial Activity of Enzymatic Products, Department of Bioscience and Biotechnology, College of Engineering, Silia University, Busan 617-736, Korea; Journal of Life Science, 2007, 17:1:1.

Rhee, et al., Isolation of a Novel Freshwater *Agarolytic cellvibrio* sp. KY-YJ-3 and Characterization of Its Extracellular β-Agarase, J. Microbiol Biotechnol, 2010, 20(1): 1378-1385; Published online Jul. 31, 2010; 8 pages.

Temuujin, et al., Overexpression and biochemical characterization of DagA from *Streptomyces coelicolor* A3(2): an endo-type β-agarase producing neoagarotetraose and neoagarohexaose, Appl Microbiol Biotechnol (2011) 92:749-759; Published online: Jun. 8, 2011, 11 pages.

* cited by examiner

*Primary Examiner* — Tekchand Saidha

(74) *Attorney, Agent, or Firm* — Blank Rome LLP

(57) ABSTRACT

The present invention relates to a composition for prevention or treatment of sepsis or septic shock, in which the composition includes neoagarooligosaccharide as an active ingredient, and the neoagarooligosaccharide according to the present invention has an excellent effect in terms of immune enhancement by effectively suppressing inflammation, and also exhibits a good effect in preventing sepsis, and therefore can be effectively used in pharmaceuticals and functional foods for prevention or treatment of sepsis or septic shock and immune enhancement.

7 Claims, 12 Drawing Sheets

Specification includes a Sequence Listing.

COMPOSITION COMPRISING NEOAGAROOLIGOSACCHARIDE AS ACTIVE INGREDIENT, FOR PREVENTION OR TREATMENT OF SEPSIS OR SEPTIC SHOCK

This application is a divisional of U.S. patent application Ser. No. 15/541,231, filed Jun. 30, 2017, which is the U.S. national stage of International Patent Application No. PCT/KR2015/009485, filed Sep. 9, 2015, which claims the benefit of Korean Patent Application No. 10-2014-0194174, filed Dec. 30, 2014, each of which is incorporated by reference.

TECHNICAL FIELD

The present invention relates to a composition for prevention or treatment of sepsis or septic shock, in which the composition includes neoagarooligosaccharide as an active ingredient.

BACKGROUND ART

For a long time, agar is a representative seaweed-derived polysaccharide which is widely used for food additives, medicines, cosmetics, livestock feed, and industrial raw materials. The agar is one of comparatively abundant fishery resources, and its yield is about 3,600 tons per year in Korea. However, only a portion of the total yield is simply processed in actual practice to be merely used as a cheap raw material, and the rest of the total yield went by wayside so that the added value is very low compared to the natural resource amount. Accordingly, there is great demand for development of a novel use of the abundant Korean agar or a study for the added value enhancement.

The agar consists of agarose and agaropectin. The agarose is formed in a straight chain structure linked by $\alpha$-1,3 bond, which is obtained by repeating agarobiose which is a monomer in which D-galactose and 3,6-anhydro-L-galactose are linked in $\beta$-1,4 bond so that the agarose's gel power is strong. On the other hand, the agaropectin is essentially composed of agarobiose units like agarose, but includes acidic group such as sulfuric acidic group so that the gel power thereof is weak.

Among them, the agarose is digested into neoagarobiose via neoagarotetraose by $\beta$-agarase acting on $\beta$-1,4 bonds, and subsequently, is finally digested into D-galactose and 3,6-anhydro-L-galactose by $\alpha$-agarase acting on the $\alpha$-1, 3 bond.

Meanwhile, *Streptomyces coelicolor* A3 (2), actinomycetes, is known to produce an extracellular agarase (which is secreted out of cells) that digests agar (Stanier et al., 1942, J. Bacteriol.; Hodgson and Chater, 1981, J. Gen. Microbiol.). The agarase is encoded by a dagA gene. The dagA gene is a beta-agarase gene whose function is the only known in actinomycetes and plays an important role in the studies on agarase production in actinomycetes. In particular, the *Streptomyces coelicolor* is the most widely used strain for the molecular biological study on actinomycetes, and the sequence of chromosomal DNA was analyzed and disclosed in the Sanger center in England in 2002.

Meanwhile, sepsis is an inflammatory reaction induced when a pathogenic gram-negative bacterium infects a living body so that a lipopolysaccharide (LPS), a component of a cell wall, acts as a toxin to result in excessive activation of an immune system of a living body. Further, sepsis may cause infectious disease in the whole body or result in a shock when symptoms are severe. Specifically, sepsis is mainly occurred when patients with underlying diseases such as malignant tumor, leukemia, malignant lymphoma, acquired immunodeficiency syndrome (AIDS), collagen disease, renal failure, liver disease, cerebrovascular disorder, diabetes or hosts with humoral immunodeficiency or cellular immunodeficiency, whose resistance is weak, such as senior and premature infant, are subject to chemotherapy of adrenal steroids or anti-neoplastic, radiation therapy such as cobalt irradiation, or treatment and surgery such as indwelling catheter, hemodialysis, organ transplantation, and cardiac disease. Sepsis is a very serious disease with a mortality rate of more than 30%, which is the main cause of death of patients hospitalized in an intensive care unit. Despite medical technology's advance, many cases of sepsis occur still due to post-operative infection in worldwide, and many cases of sepsis occur when a person with weak immunity of the body, such as neonates or seniors, is infected. Typically, the birth sepsis is known to develop in about 3 of 1,000 mature infants, but premature infants are known to increase the attack rate by 3 to 4 times. When a patient has sepsis, the patient is usually treated with antibiotics. However, when microorganisms are proliferated since the suitable treatment is delayed, or when the infection is caused by a strain resistant to antibiotics, antibiotics only may not effectively treat the disease, and the number of pathogens resistant to various antibiotics is increasing. Thus, it is urgently needed to develop a novel therapeutic agent for sepsis The inventors of the present invention have extensively studied to meet the requirements. As a result, the inventors have found that agar-derived neoagarooligosaccharide prepared by the DagA enzyme reaction has excellent effects that not only inhibits the growth of bacteria, but also eliminates the endotoxin isolated from dead bacteria. Thus, it is used in combination with antibiotics so as to minimize the side effects caused by antibiotics and to have remarkably excellent effects of treating sepsis compared to the single administration therewith, thereby completing the present invention.

DISCLOSURE

Technical Problem

An object of the present invention relates to a composition for prevention or treatment of sepsis or septic shock, in which the composition includes neoagarooligosaccharide as an active ingredient.

Another object of the present invention relates to a composition for reinforcement of immunization, in which the composition includes neoagarooligosaccharide as an active ingredient.

Technical Solution

In order to address the issues as described above, the present invention provides a pharmaceutical composition for prevention or treatment of sepsis or septic shock, in which the pharmaceutical composition includes neoagarooligosaccharide as an active ingredient.

Further, the present invention provides a food composition for prevention or amelioration of sepsis or septic shock, in which the food composition includes neoagarooligosaccharide as an active ingredient.

Further, the present invention provides a pharmaceutical composition for reinforcement of immunization, in which the pharmaceutical composition includes neoagarooligosaccharide as an active ingredient.

Further, the present invention provides a functional food for reinforcement of immunization, in which the functional food includes neoagarooligosaccharide as an active ingredient.

Advantageous Effects

Since the neoagarooligosaccharide according to the present invention shows excellent effects of not only preventing sepsis, but also enhancing immunity by effectively suppressing inflammation development, the neoagarooligosaccharide is useful for medicines and functional foods for prevention or treatment of sepsis or septic shock and reinforcement of immunization.

BEST MODES OF THE INVENTION

Figure 1:
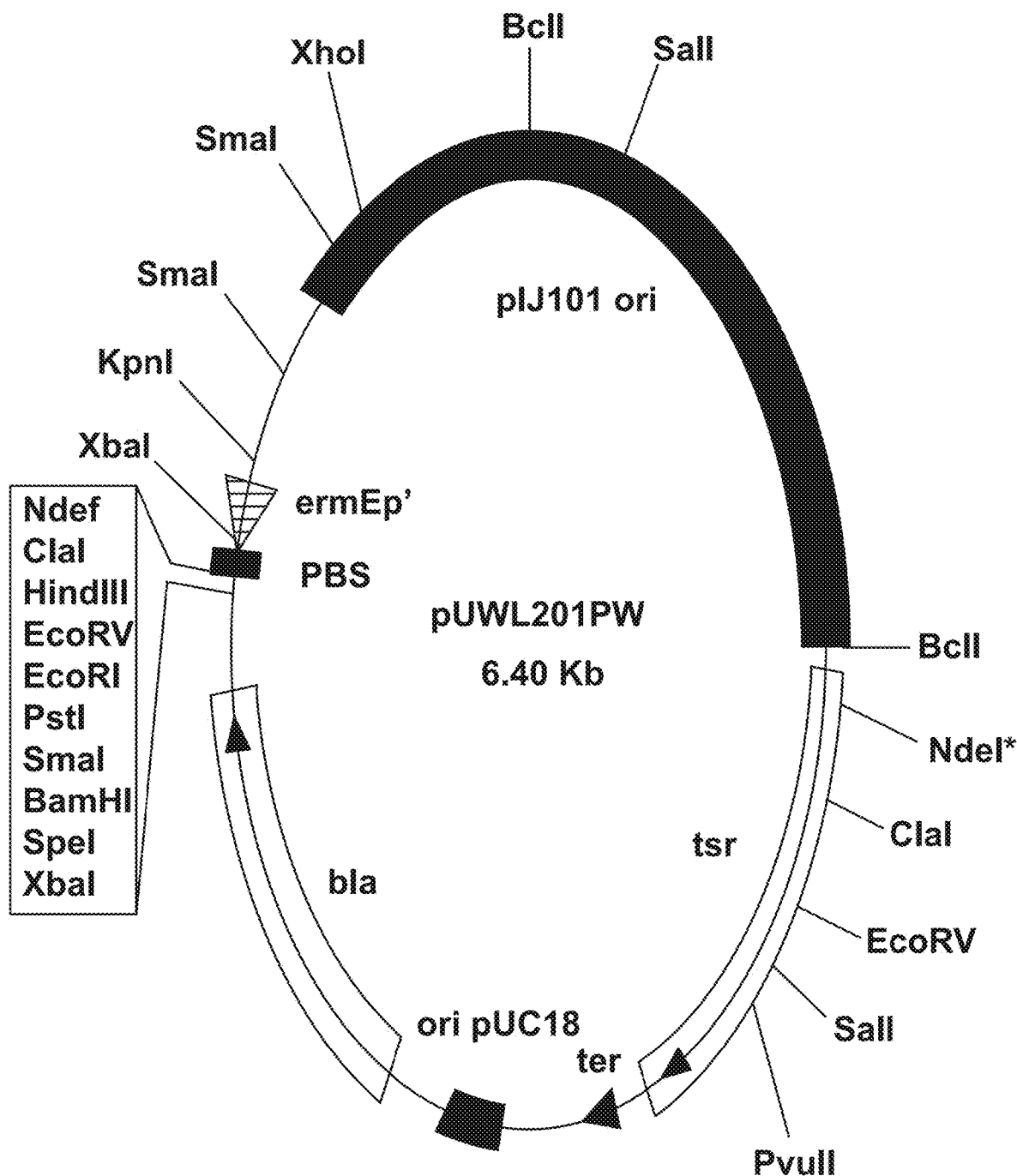
FIG. 1 shows a map of pUWL201pw vector.

Hereinafter, the present invention will be described in detail.

The present invention provides a composition for prevention or treatment of sepsis or septic shock, in which the composition includes neoagarooligosaccharide, which is prepared from agar or agarose by a DagA enzyme reaction, as an active ingredient.

The composition includes a pharmaceutical composition and a food composition.

DagA of the present invention is a β-agarase protein, which means the amino acid sequence of SEQ ID NO: 2. DagA includes a protein produced from *Streptomyces coelicolor* which is actinomycetes, or a heterologous strain. Further, DagA includes a recombinant protein according to conventional gene recombinant methods within the range that the function is not changed to be completely different or the beta-agarase activity is not lost, i.e., a method of including a labeled amino acid for advantageous purification, modifying the amino acid sequence for heterologous expression, etc.

More specifically, DagA of the present invention is produced with a molecular weight of about 35 kDa, having 309 amino acids of SEQ ID NO: 2 when it is translated from a gene of beta-agarase prepared by *Streptomyces coelicolor*. DaeA is secreted in the form of the completed extracellular protein (about 32 kDa) in which 30 N-terminal amino acid signal peptides are cleaved to have the amino acid sequence 31 to 309 of SEQ ID NO: 2.

The dagA gene of *Streptomyces coelicolor* may encode the DagA, and the dagA gene may be represented by the nucleotide sequence of SEQ ID NO: 1. SEQ ID NO: 1 is the nucleotide sequence of the gene present in the genome of *Streptomyces coelicolor* A3 (2) and is named "SC03471" on database of National Center for Biotechnology Information (NCBI) in U.S. As confirmed through in vitro experiments, the transcription of the dagA gene is regulated by 4 or 5 other promoters that are recognized by at least 3 other holoenzymes of the RNA polymerase. Through an analysis of transcription step of the dagA gene, the transcription was shown to be initiated at the 32nd, 77th, 125th, and 220th bases of the encoding sequence.

DagA of the present invention may be prepared through the culture of *Streptomyces coelicolor*, which is a producing strain of DagA, but the expression system of *Streptomyces lividans*, a heterologous strain is preferably used to increase production efficiency. A method is used in which the dagA gene is inserted into a vector for *actinomyces* to prepare a recombinant vector, then *Streptomyces lividans* is transformed with the recombinant vector, and then the transformant is cultured. In this case, the recombinant vector is preferably configured in which the transcription of the dagA gene can be regulated by a promoter derived from actinomycetes.

When preparing the recombinant vector, the promoter derived from actinomycetes can be selected and used since the promoter derived from actinomycetes includes various promoters such as a sgtR promoter (sgtRp), an ermE promoter (ermEp), and a tipA promoter (tipAp). Several kinds of vectors configured in which the transcription may be regulated by these promoters have been developed so that SC03471 is cloned into this vector to produce a recombinant vector having a structure in which the transcription is regulated by the promoter derived from actinomycetes.

A host strain may be transformed with a recombinant vector to prepare the transformant. Since there are various methods for transformation according to the host strain, an appropriate method can be selected and used. For example, when *Streptomyces lividans* is used as a host strain, a transformation method can use PEG (polyethylene glycol) as a medium.

A DagA producing strain such as a transformant may be cultured in a liquid medium to prepare DagA. High purity DagA can be prepared using a conventional protein purification method such as ultrafiltration for the obtained culture medium. At this time, agar or agarose is included in the liquid medium so as to prepare DagA more efficiently.

The polysaccharide such as agar and agarose may be converted into relatively small oligosaccharides through the enzyme reaction of DagA. The enzyme reaction is preferably performed at a temperature of 35° C. to 45° C. and a pH of 6 to 8, but is not limited thereto.

The neoagarooligosaccharide is prepared as a product obtained by the enzyme reaction, and the neoagarooligosaccharide may be each of neoagarobiose, neoagarotetraose, and neoagarohexaose, and they may be in a mixed state thereof, but is not limited thereto.

The neoagarooligosaccharide according to the present invention shows preventive or therapeutic effects of sepsis by reducing pro-inflammatory cytokines, increasing anti-inflammatory cytokines, and significantly lowering the mortality due to sepsis or septic shock.

In the present invention, "sepsis" refers to a state in which infection causes a serious inflammatory reaction with a microorganism in a whole body. Systemic inflammatory response syndrome (SIRS) is called when there are two or more kinds of symptoms such as fever with body temperature of 38° C. or more, hypothermia down to 36° C., respiratory rate increased more than 24 times per minute (tachypnea), at least 90 heartbeats per minute (tachycardia), and an increase or marked decrease in leukocyte count on the blood test. Sepsis is called when the systemic inflammatory response syndrome is caused by microbial infection. Pathogens consistently or intermittently enter the bloodstream from the body's infectious focuses, settle in various organs, create lesions, and show severe systemic symptoms. The causative bacteria include *staphylococcus, streptococcus, Escherichia coli, Pseudomonas aeruginosa, Mycobacterium tuberculosis, pneumococcus*, fungus, and anaerobic bacteria.

Further, the present invention provides a composition for reinforcement of immunization, in which the composition includes neoagarooligosaccharide, which is prepared from agar or agarose by a DagA enzyme reaction, as an active ingredient.

The composition includes a pharmaceutical composition and a health supplement food.

The neoagarooligosaccharide according to the present invention exhibits an effect of reinforcement of immunization by inhibiting the secretion of pro-inflammatory cytokines and increasing the secretion of anti-inflammatory cytokines.

The composition may be used for an immunological disease or the prevention of the immunological disease. The immunological disease includes various inflammatory diseases, allergic diseases and cancers caused by abnormal immune system of living body. Examples of the immunological diseases include cold, asthma, pneumonia, allergic rhinitis, allergic conjunctivitis, atopic dermatitis, allergies, rheumatoid arthritis, Alzheimer's disease, autoimmune thyroid disease, inflammatory bowel disease, aplastic anemia, lupus erythematosus, and psoriasis, but are not limited thereto.

Since the neoagarooligosaccharide according to the present invention shows excellent effects of not only preventing sepsis, but also enhancing immunity, the neoagarooligosaccharide is useful for medicines and functional foods for prevention or treatment of sepsis or septic shock and reinforcement of immunization.

The composition of the present invention may further include suitable carriers, excipients, and diluents which are conventionally used in the preparation of pharmaceutical compositions. The pharmaceutical composition according to the present invention may be formulated and used in the form of oral formulations, external preparations, suppositories, and sterilized injections such as powders, granules, tablets, capsules, suspensions, emulsions, syrups and aerosols. Suitable formulations known in the art may preferably include those disclosed in Remington's Pharmaceutical Sciences, Mack Publishing Company, Easton Pa.

The pharmaceutical composition of the present invention may include carriers, excipients and diluents such as lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oil.

When the pharmaceutical composition of the present invention is formulated, it is prepared using diluents or excipients such as fillers, extenders, binders, wetting agents, disintegrants, and surfactants which are usually used. Solid formulations for oral administration include tablets, pills, powders, granules, capsules, and the like. These solid formulations may be prepared by mixing at least one excipient such as starch, calcium carbonate, sucrose, lactose, and gelatin. In addition to simple excipients, lubricants such as magnesium stearate and talc are also used. Liquid formulations for oral administration may include suspensions, solutions, emulsions, syrups and the like, and may include various excipients such as wetting agents, sweeteners, fragrances, preservatives and the like in addition to water and liquid paraffin which are simple diluents commonly used. Formulations for parenteral administration include sterilized aqueous solutions, non-aqueous solutions, suspensions, emulsions, freeze-dried formulations, and suppositories. The non-aqueous solvent and suspension may include propylene glycol, polyethylene glycol, vegetable oil such as olive oil, injectable ester such as ethyl oleate, and the like. Bases of suppository may include witepsol, macrogol, tween 61, cacao butter, laurin, glycerogelatin and the like.

The term "administration" as used herein refers to provide any composition of the present invention to a subject in any suitable manner.

The preferred dosage of the pharmaceutical composition of the present invention varies depending on the condition and body weight of the subject, the degree of disease, the type of drug, the administration route, and the period of time, but may be appropriately selected by those skilled in the art. In order for a desired effect, the composition of the present invention may be administered at 0.001 mg/kg to 1000 mg/kg per one day. The administration may be carried out once a day or divided into several times. The dose does not limit the scope of the present invention in any way.

The pharmaceutical composition of the present invention may be administered to a subject through various pathways. All ways of administration may be expected to include, for example, oral, rectal or intravenous, intramuscular, subcutaneous, uterine duramater, or intracerebral injection administration. The pharmaceutical composition of the present invention may preferably be administered in the form of an injection.

The pharmaceutical composition according to the present invention may further include the above-mentioned effective ingredient as well as at least one known substance having effects of preventing or treating sepsis or septic shock or enhancing immunization.

The pharmaceutical composition according to the present invention may further include a bronchodilator, an antihistamine agent or an anti-inflammatory agent in addition to the above-mentioned active ingredients.

For example, the bronchodilator may include β-agonist, an anticholinergic agent, a methylantanine, etc. The antihistamines may include acrivastine, cetirizine, desloratadine, fexofenadine, levocertirizine, loratadine, mizolastine, ailmemazine, chlocertirizine, clemastine, cyproheptadine, hydroxyzine, ketotifen, promenthazine, and the like. The anti-inflammatory agent may include aspirin, diclofenac, fenoprofen, flurbiprofen, ibuprofen, indomethacin, ketoprofen, naproxen, piroxicam, sulindac, celecoxib, valdecoxib, rofecoxib, and the like.

In the present invention, the term "functional food" refers to a food group in which food is imparted with added value to allow the function of the food to function or express for particular purpose using physical, biochemical, biotechnological techniques or the like, or food which is designed and manufactured so that the body control function related to the regulation of the bio-defense rhythm of the food composition, disease prevention and recovery, etc. is sufficiently expressed in the living body.

The functional food may include a food supplement additive which is acceptable in sitology, and may further include suitable carriers, excipients and diluents conventionally used in the production of functional foods.

When the composition of the present invention is used as a food additive, the composition may be added individually or may be used together with other food or food ingredients, and may be suitably used according to a conventional method. The amount of the active ingredient to be mixed can be suitably determined according to the intended use (e.g., prevention, health or therapeutic treatment). In the production of food or beverage, the composition of the present invention is generally added in an amount of 15% or less by weight, preferably 10% or less by weight based on the raw material. However, it may be less than the above range on long-term intake for the purpose of health and hygiene, or for the purpose of controlling health. The active ingredient may be used in an amount exceeding the above range due to no problem in aspects of safety.

In addition to the above, the composition of the present invention may further include various nutrients, vitamins, electrolytes, flavors, colorants, pectic acid and its salt, alginic acid and its salts, organic acids, protective colloid thickening agents, pH adjusting agents, stabilizers, preservatives, glycerin, alcohols, carbonating agents used in carbonates, and the like. In addition, the composition of the present invention may include flesh for the production of natural fruit juices, fruit juice drinks and vegetable drinks. These components may be used independently or in combination. The proportion of such additives does not matter, but is generally selected in the range of 0.01 parts by weight to 0.1 parts by weight per 100 parts by weight of the composition of the present invention.

MODES OF THE INVENTION

Hereinafter, the present invention will be described in more detail with reference to Embodiments. However, it should be noted that the following Embodiments are provided to illustrate the present invention to allow a more easily understanding, but the present invention is not limited to Embodiments.

Embodiment 1: Production of DagA

Figure 2:
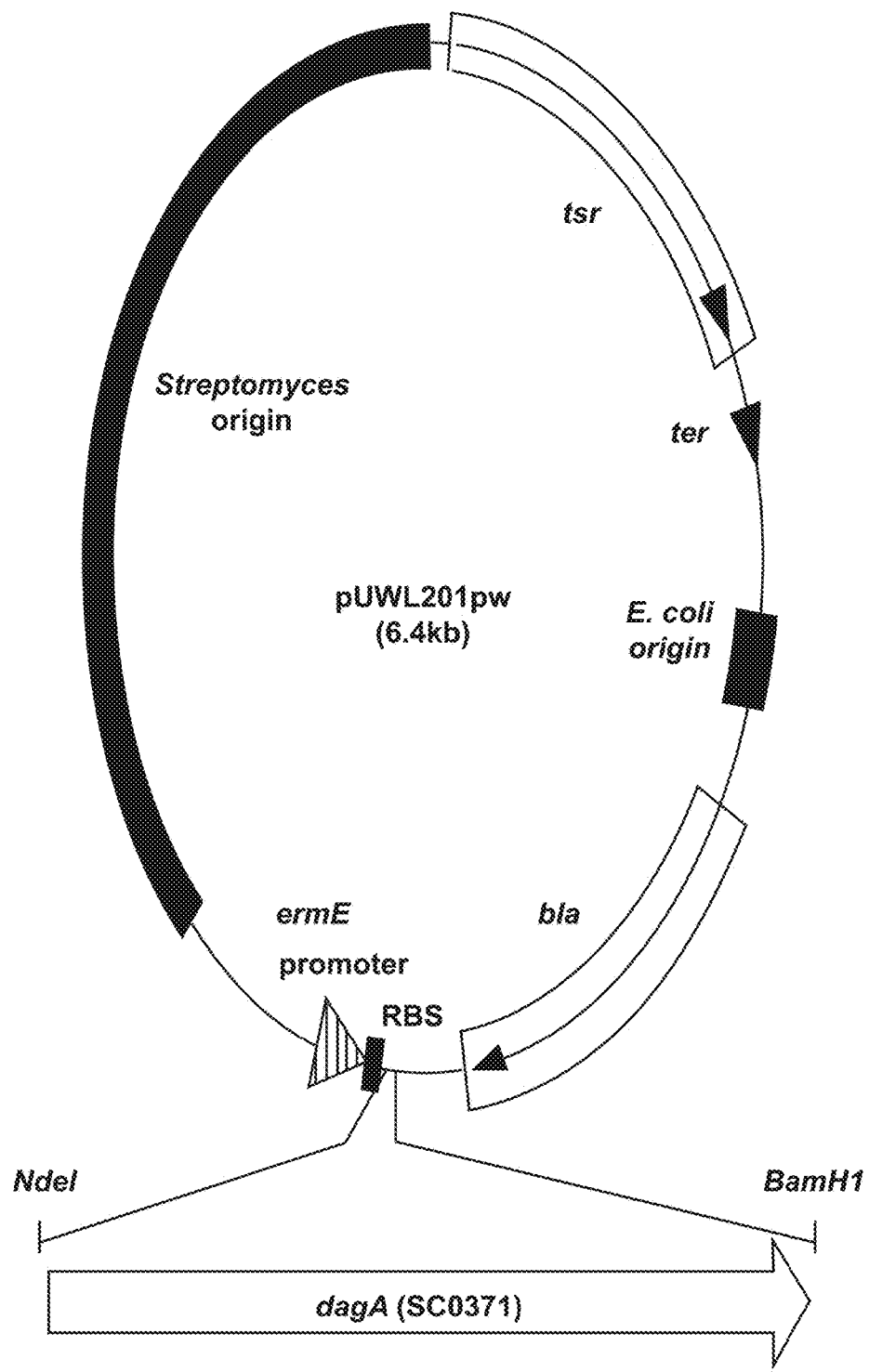
FIG. 2 shows a map of a recombination vector according to an embodiment of the present invention.

PCR was carried out using the following Asm-F and Asm-R primers with the chromosomal DNA of *Streptomyces coelicolor* A3 (2) as a template to amplify a dagA gene fragment (a 947 bp fragment in which a signal peptide and a complete peptide of DagA were encoded, and a partial sequence of the primer was included in SEQ ID NO: 1). The dagA gene was cloned into the pUWL201pw vector shown in FIG. 1 using the restriction enzyme site (NdeI/BamHI) of the fragment, and thus a recombinant vector was prepared such that the transcription of the dagA gene was regulated by the ermE promoter. Such configuration is illustrated in FIG. 2.

```
Asm-F primer:
                                        (SEQ ID NO: 3)
5'-GACATATGGTGGTCAACCGACGTGATC-3' (NdeI)

Asm-R primer:
                                        (SEQ ID NO: 4)
5'-GGTGGATCCCTACACGGCCTGATACG-3' (BamHI)
```

The transformant strain obtained by transforming *Streptomyces lividans* TK24 with the recombinant vector was used for the preparation of DagA.

The strain was inoculated on R2YE liquid medium containing 0.3% (w/v) of agar and cultured and shaken at 120 rpm and 28° C. for 48 hours to 72 hours. After the pre-culture, the culture was performed, and each time of the culture was 2.5 days. The culture solution obtained through the culture was centrifuged to remove microbial cells, and the supernatant was filtered through an ultrafiltration membrane (5 kDa cut-off membrane) to isolate and purify proteins that did not pass through the filtration membrane. The obtained concentrate (enzyme solution) was used while being stored by freeze drying.

Embodiment 2: Measurement of Agarase Activity of DagA

The agarase activity of DagA in Embodiment 1 was measured using estimation of reducing sugar by DNS method. 0.5 ml of a 20 mM Tris-HCl solution (pH 7) containing 0.5% (w/v) of agarose was mixed with 10 μl of the enzyme solution obtained in Embodiment 1, and the mixture was reacted at 40° C. for 15 minutes. Then, 0.5 ml of DNS reagent (dinitrosalicylic acid 6.5 G, 2M NaOH 325 ml, glycerol 45 ml/1 l distilled water) was added thereto, and the mixture was boiled for 10 minutes. Then, the mixture was cooled, and the absorbance thereof was measured at Å540 nm. 1 U of the enzyme was defined as an activity that shows an absorbance (Å540 nm) of 0.001 after 15 minutes of reaction.

Embodiment 3. Degradation of Agar or Agarose by DagA Enzyme Reaction

1 L of a 20 mM Tris-HCl solution in which 0.5% to 5% (w/v) of agar or agarose was dissolved was prepared and heated at 100° C. for about 10 minutes to dissolve it sufficiently. Then, the mixture was cooled down to 40° C. and then was treated with 2,000 U to 50,000 U of DagA enzyme to perform the enzyme reaction for 24 hours.

In order to remove undegraded agarose from the enzyme reaction product, supernatant was recollected by centrifugation, and then the enzyme reaction product was confirmed using thin layer chromatography (TLC). The recollected supernatant was partially purified by ultrafiltration with a 5 kDa cut-off membrane.

Embodiment 4: Confirmation of DagA Enzyme Reaction Product Composition by HPLC-ELSD Analysis HPLC-ELSD analysis was performed to confirm the composition of the enzyme reaction product obtained in Embodiment 3 as described above. NH2 P-50 4E multimode column (250×4.6 mm) was used, and a mixed solution of acetonitrile and water (acetonitrile:water=65:35) was used as a mobile phase. The result is illustrated in FIG. 3.

Figure 3:
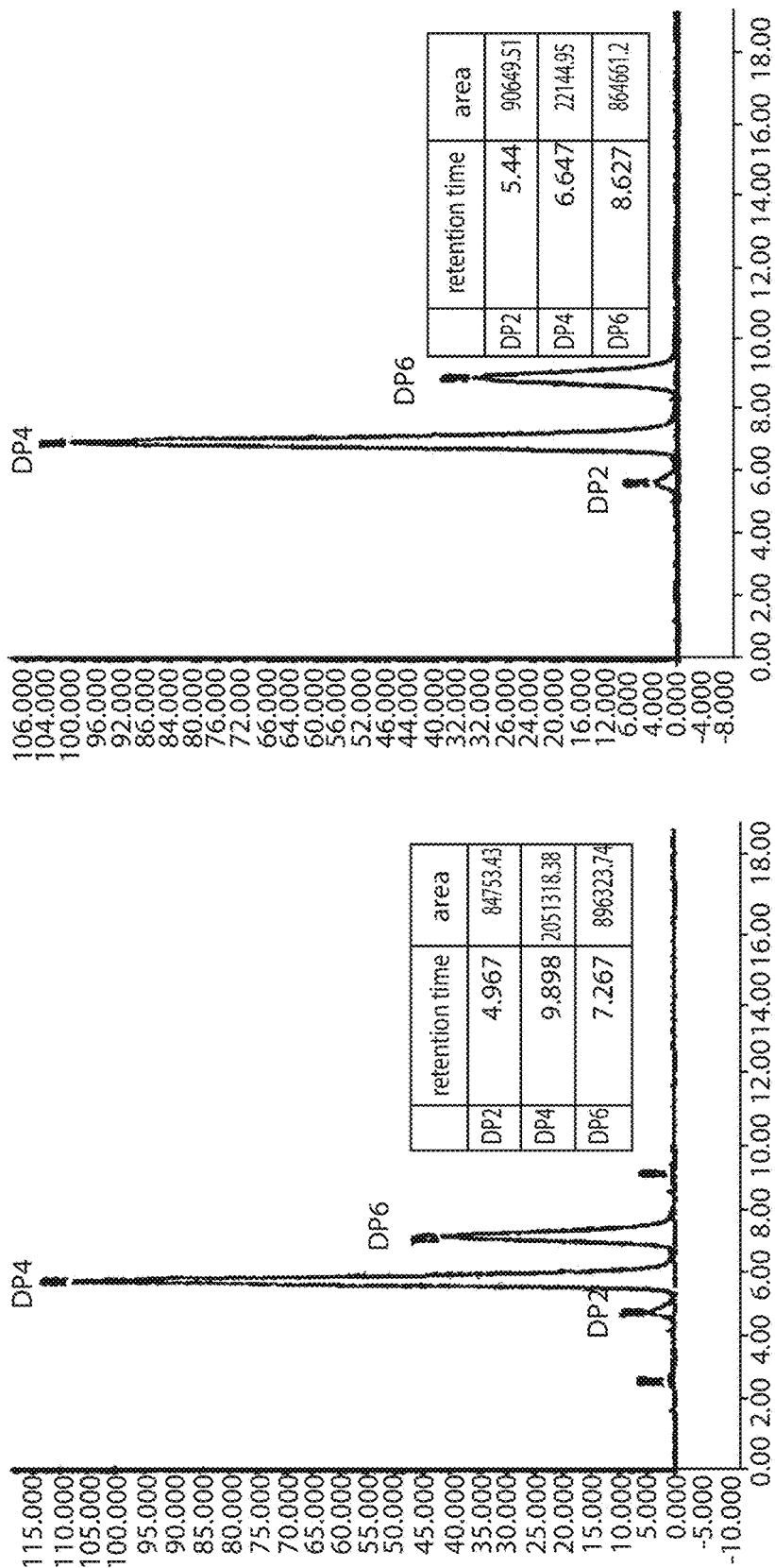
FIG. 3 shows graphs illustrating results of an HPLC-ELSD analysis of an enzyme reaction product of the present invention.
Figure 3:
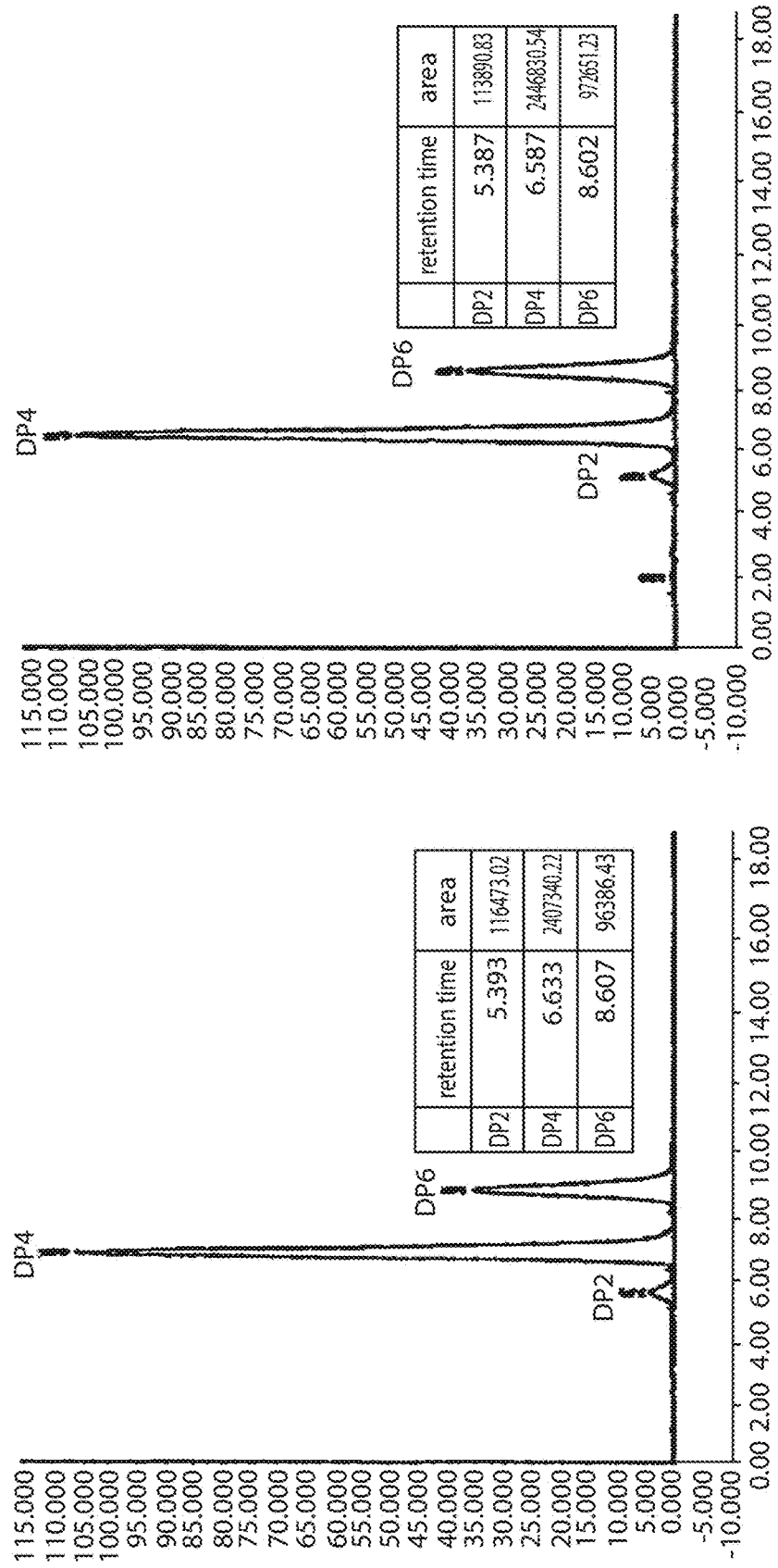

As shown in FIG. 3, the total amount of neoagarooligosaccharides composed of neoagarobiose (hereinafter referred to as "DP2"), neoagarotetraose (hereinafter referred to as "DP4"), and neoagarohexaose (hereinafter referred to as "DP4") of the reaction products was showed to account for 65±20% (by weight). DP2, DP4, and DP6 respectively were showed to account for 0% to 10%, 50% to 70%, and 30% to 50% (by weight) based on the total amount of the neoagarooligosaccharides.

Experimental Example 1: Analysis of Preventive Effect on Sepsis by Administration of Neoagarooligosaccharide In order to analyze the preventive effect of neoagarooligosaccharide administration on sepsis, the following experiment was conducted.

1-1. Experimental Design and Survival Rate Analysis

Figure 4:
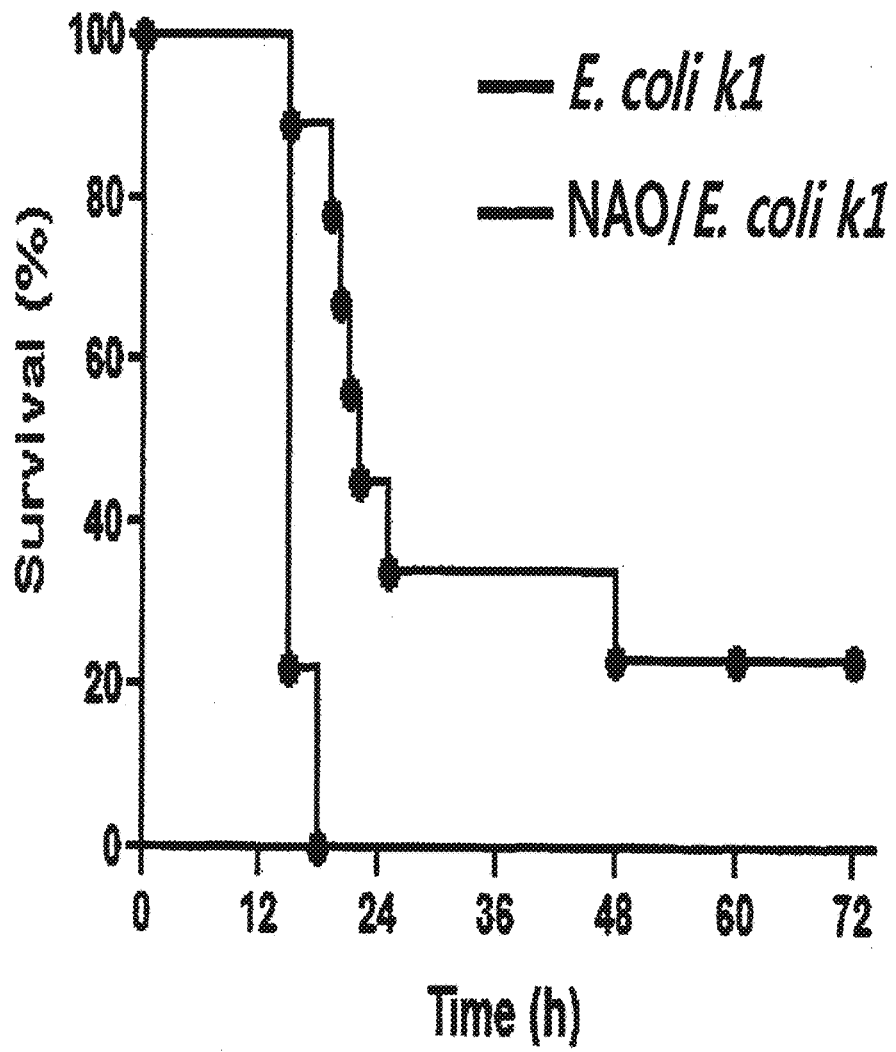
FIG. 4 is a graph showing the survival rate over time of animal models in which neoagarooligosaccharide of the present invention is pre-treated and sepsis is induced.

Six-week-old female BALB/c mice were used as experimental animals. The mice were pretreated intraperitoneally with neoagarooligosaccharide on mouse abdomen. One hour later, $10^7$ CFU/mice of *E. coli* K1 (dissolved in LB broth) was injected to induce sepsis. FIG. 4 shows the survival rate over time of each mouse in the experimental group and the control group in which sepsis was induced.

As shown in FIG. 4, the control group died 18 hours after the induction of sepsis. On the other hand, the survival rate of the group which was pretreated with neoagarooligosaccharide was significantly increased compared to that of the control group.

1-2. Analysis of Serum

The serum was separated from each mouse 12 hours after the induction of sepsis to analyze levels of inflammatory cytokines (TNF-α, IL-6, IL-1β, IL-12p70, and IL-10), AST, ALT, and BUN, respectively, in the serum. At this time, the concentration of the cytokine was measured using an ELISA kit (eBiosciences, San Diego, Calif.), and the result are shown in FIGS. 5 and 6.

Figure 5:
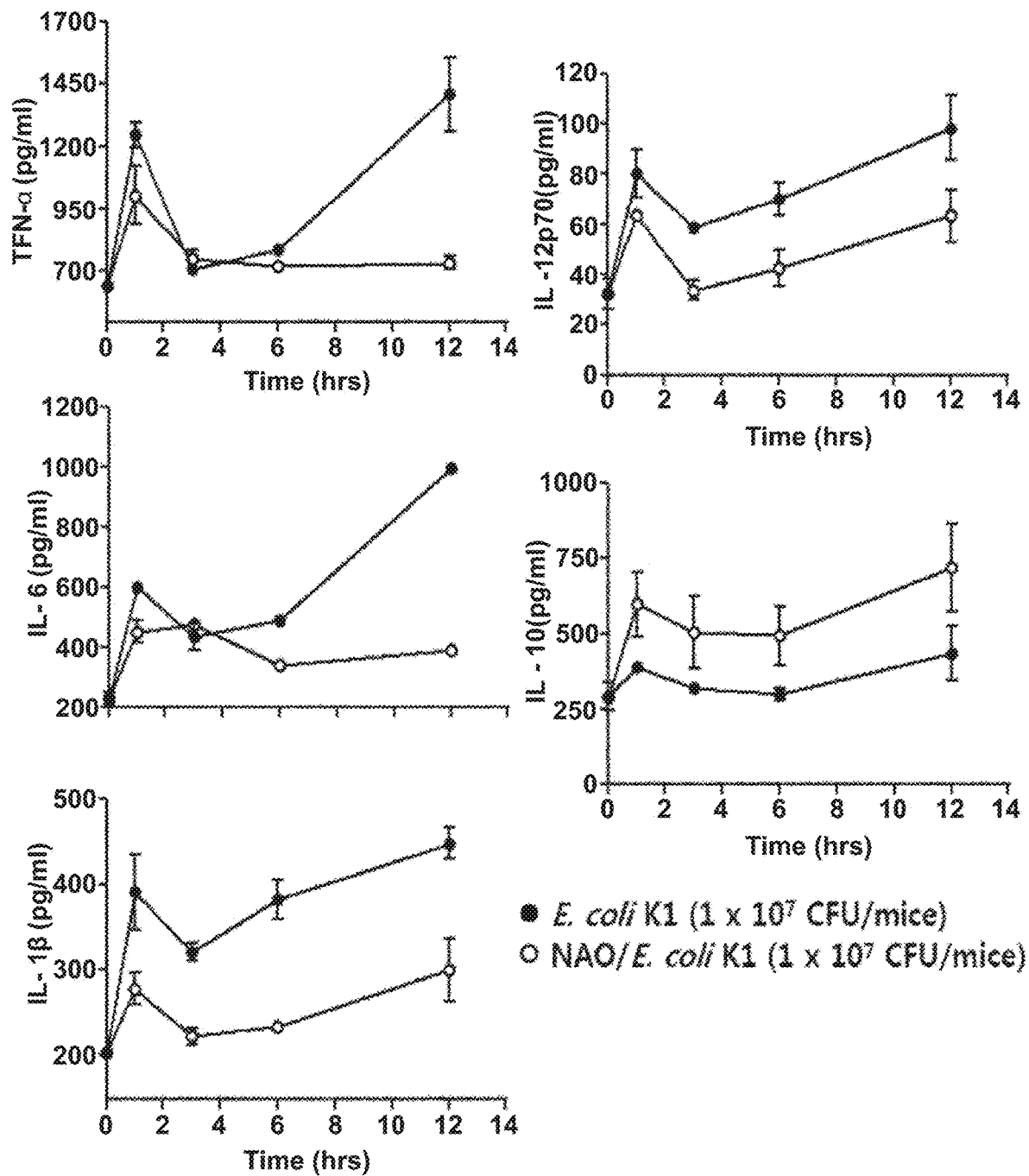
FIG. 5 is a graph showing the secretion amount of inflammatory cytokines in the serum of animal models in which neoagarooligosaccharide of the present invention is pre-treated and sepsis is induced.

As shown in FIG. 5, when pre-treated with neoagarooligosaccharide, the amounts of TNF-α, IL-6, IL-1β and IL-12p70, which are pro-inflammatory cytokines increased by sepsis in the mouse serum, were significantly inhibited. On the other hand, the secretion of IL-10, an anti-inflammatory cytokine, was increased by pre-treatment of neoagarooligosaccharide.

Figure 6:
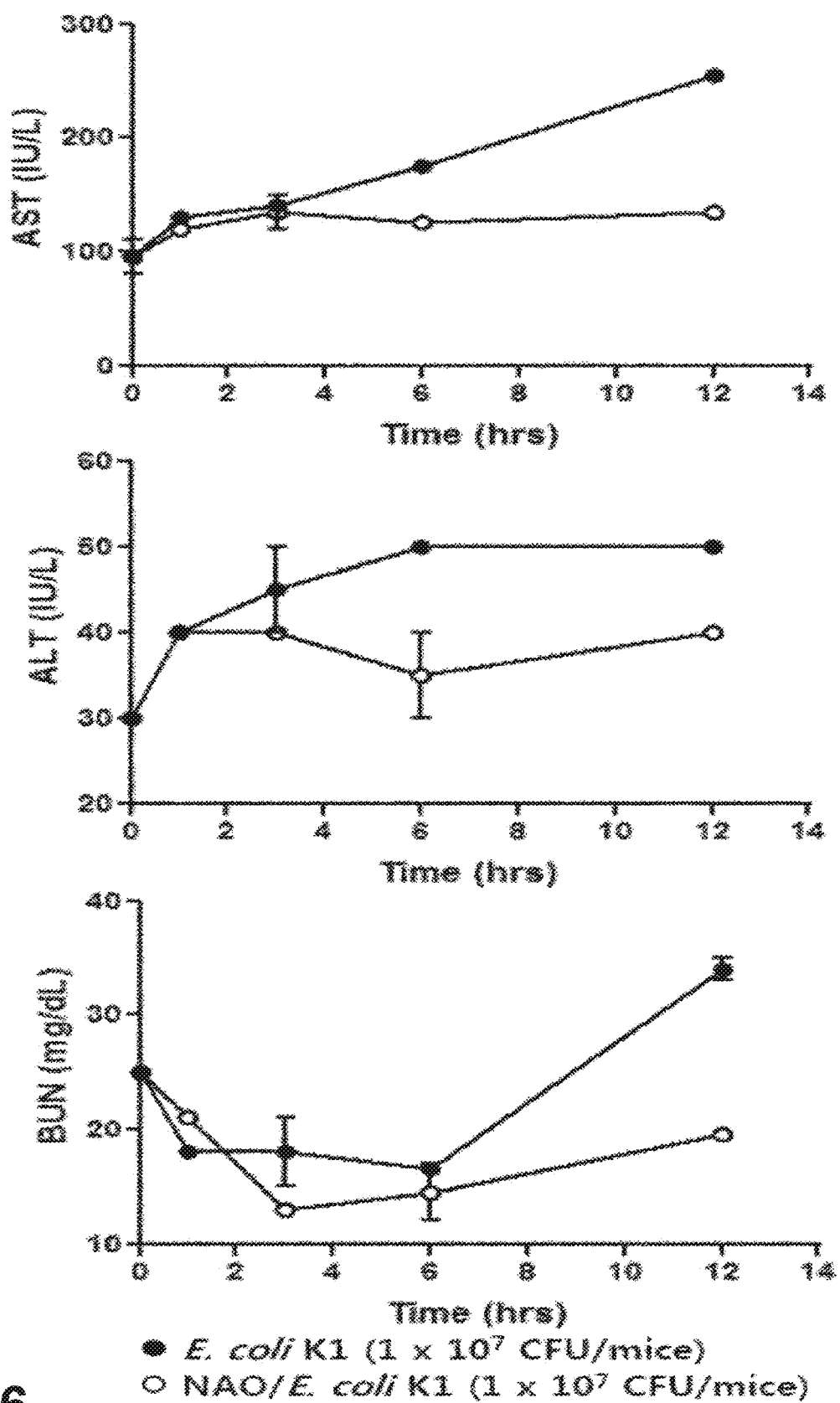
FIG. 6 is a graph showing AST, ALT and BUN concentrations in the serum of animal models in which neoagarooligosaccharide of the present invention is pre-treated and sepsis is induced.

Further, as shown in FIG. 6, the concentrations of AST, ALT, and BUN in the serum, which were associated with hepatic and renal toxicity, were increased by sepsis, but were significantly inhibited when the mouse was pre-treated with neoagarooligosaccharide.

Experimental Example 2: Analysis of Effect of Neoagarooligosaccharide on the Immune Enhancement In order to analyze the effect of neoagarooligosaccharide on the immunity enhancement, the following experiment was performed.

2-1. Experimental Design and Survival Rate Analysis

Figure 7:
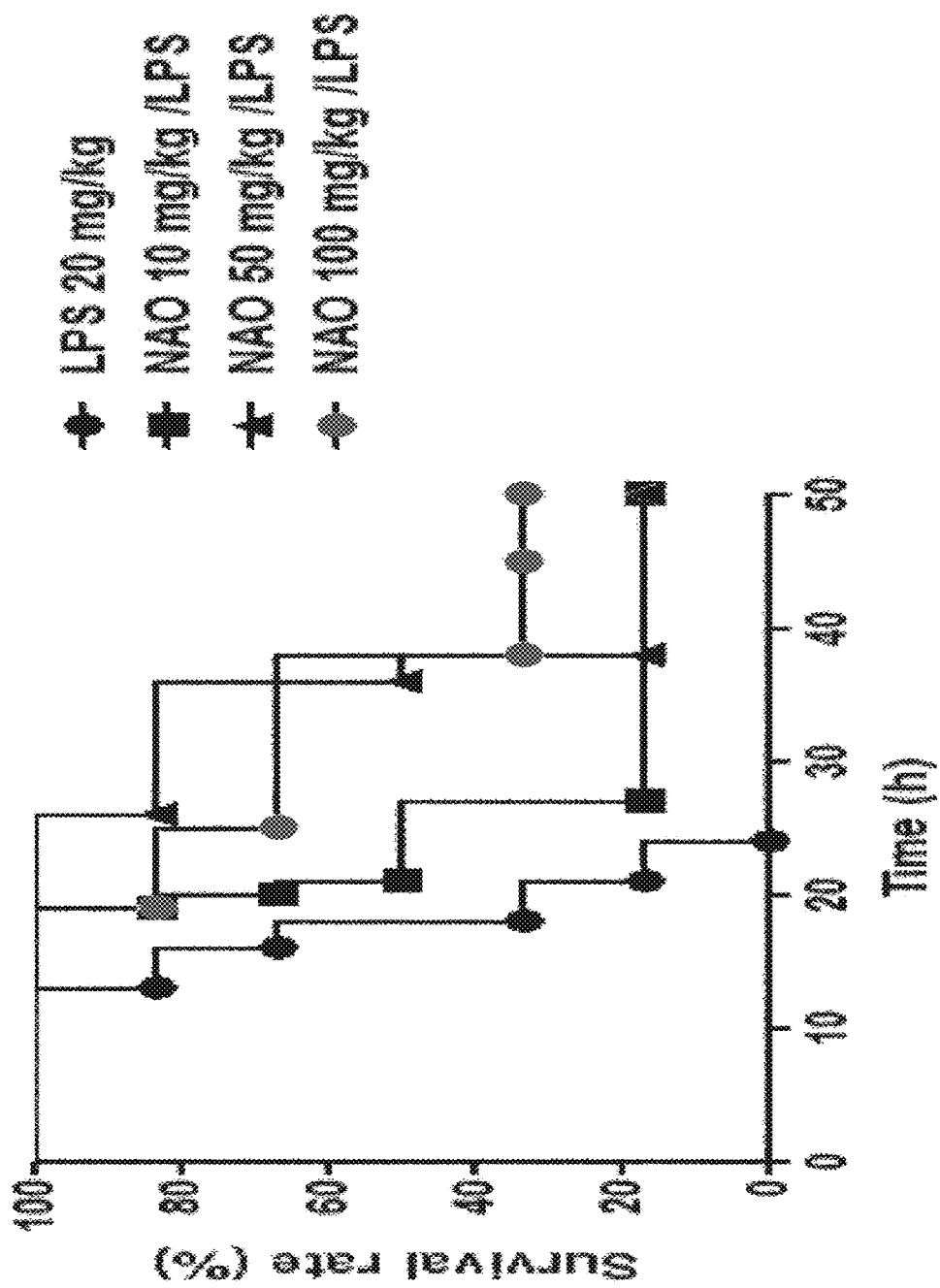
FIG. 7 is a graph showing the survival rate of animal models in which neoagarooligosaccharide of the present invention is pre-treated and LPS is administered.

Six-week-old female BALB/c mice were used as experimental animals. The mice were pretreated intraperitoneally with 100 mg/kg of neoagarooligosaccharide on mouse abdomen and injected with 20 mg/kg of lipopolysaccharide (LPS) after one hour. FIG. 7 shows the survival rate over time of each mouse in the experimental group and the control group.

As shown in FIG. 7, the control group died 24 hours after administration of LPS. On the other hand, the survival rate of the group pretreated with neoagarooligosaccharide was significantly increased compared to that of the control group. The survival rate was increased depending on the concentration of neoagarooligosaccharide.

2-2. Analysis of Serum

The serum was separated from each mouse 12 hours after LPS administration to analyze levels of inflammatory cytokines (TNF-α, IL-6, IL-1β, IL-12p70, and IL-10), AST, ALT, and BUN, respectively, in the serum. At this time, the concentrations of the cytokines were measured using an ELISA kit (eBiosciences, San Diego, Calif.), and the result are shown in FIGS. 8 and 9.

Figure 8:
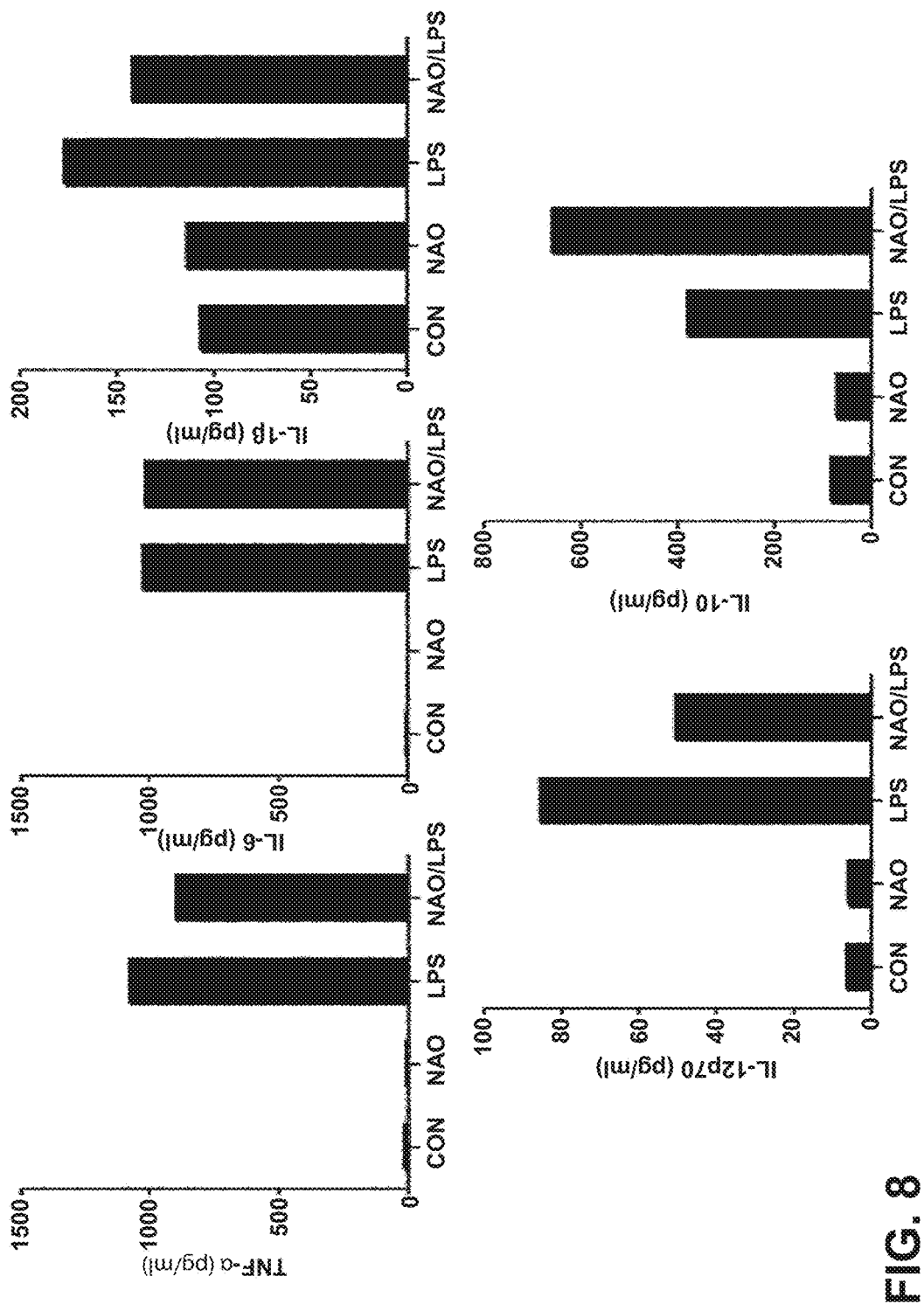
FIG. 8 is a graph showing the secretion amount of inflammatory cytokine in serum of animal models in which neoagarooligosaccharide of the present invention is pre-treated and LPS is administered.

As shown in FIG. 8, when pre-treated with neoagarooligosaccharide, the amounts of TNF-α, IL-6, IL-1β, and IL-12p70, which are pro-inflammatory cytokines increased by LPS administration in the mouse serum, were significantly inhibited. On the other hand, the secretion of IL-10, an anti-inflammatory cytokine, was increased by pre-treatment of neoagarooligosaccharide.

Figure 9:
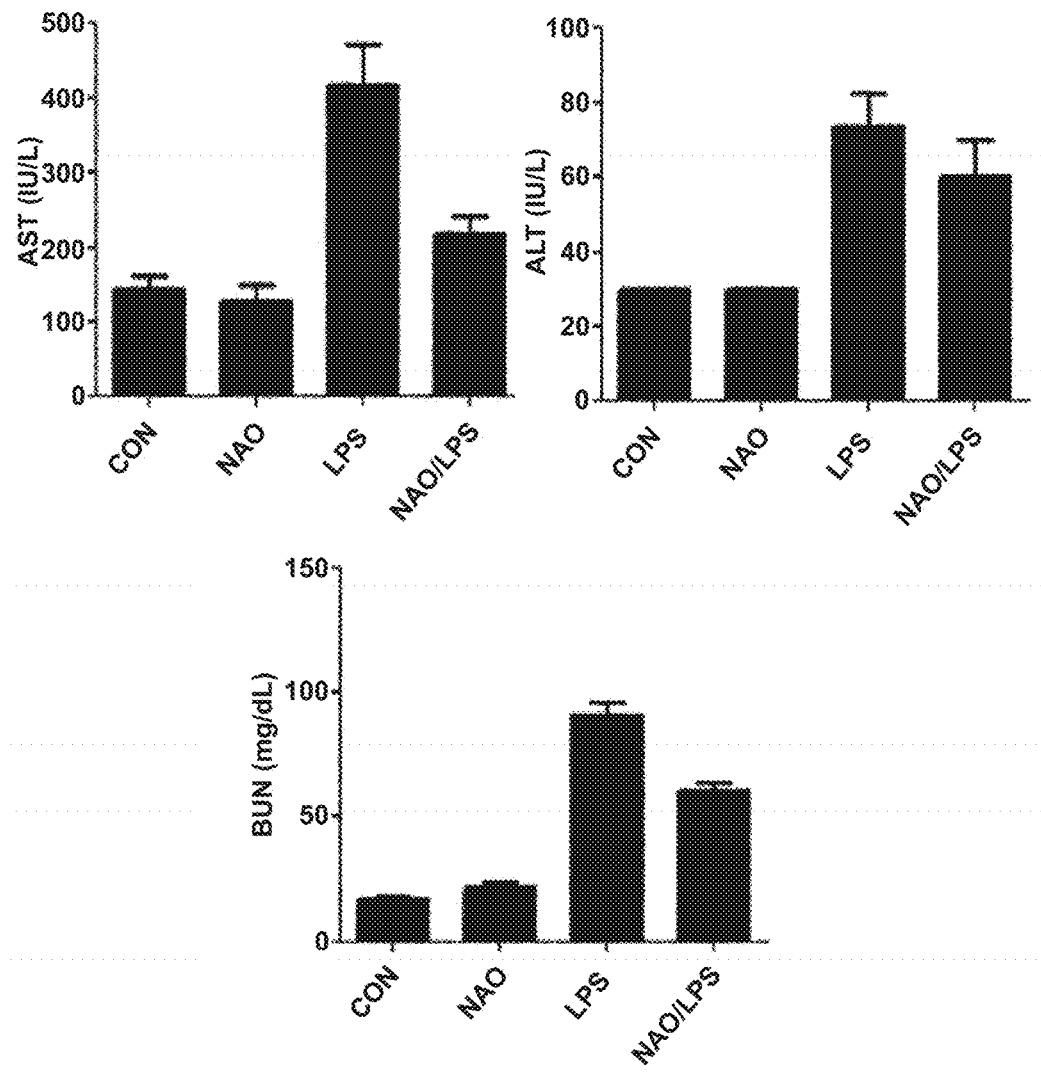
FIG. 9 is a graph showing AST, ALT and BUN concentrations in the serum of animal models in which neoagarooligosaccharide of the present invention is pre-treated and LPS is administered.

Further, as shown in FIG. 9, the concentrations of AST, ALT, and BUN in the serum, which were associated with hepatic and renal toxicity, were increased by sepsis, but were significantly decreased when the mouse was pre-treated with neoagarooligosaccharide.

2-3. Analysis of Organization

The lung and spleen tissues were extracted from each mouse after 12 hours of the administration of LPS. Paraffin section and H&E staining were performed according to a conventionally known method to observe them through a microscope. The results are shown in FIGS. 10 and 11.

Figure 10:
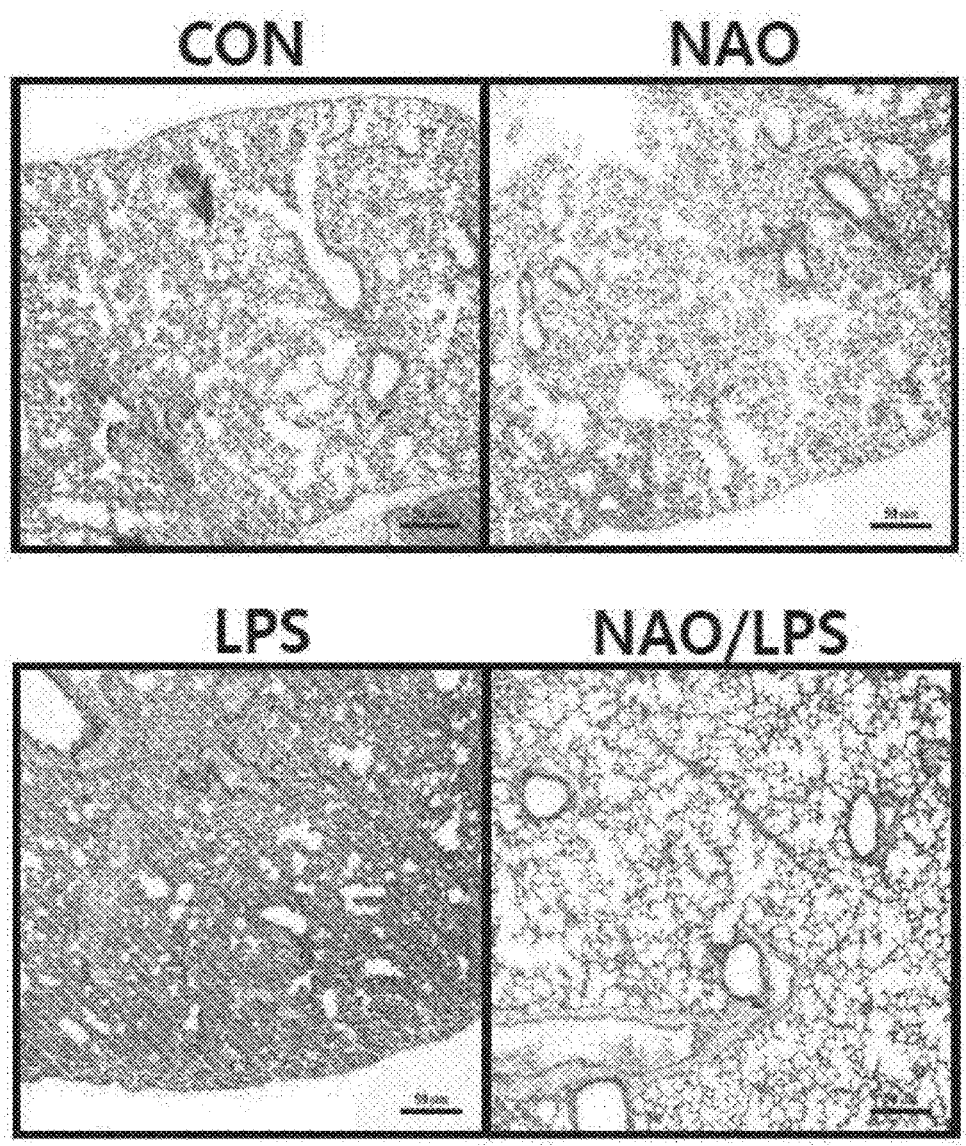
FIG. 10 is a graph showing the degree of infiltration of inflammatory inducing cells in the lung tissue of animal models in which neoagarooligosaccharide of the present invention is pre-treated and LPS is administered.

As shown in FIG. 10, the infiltration of inflammatory cells in the lung tissue, in which the neoagarooligosaccharide was pretreated was significantly inhibited compared to that of the control group.

Figure 11:
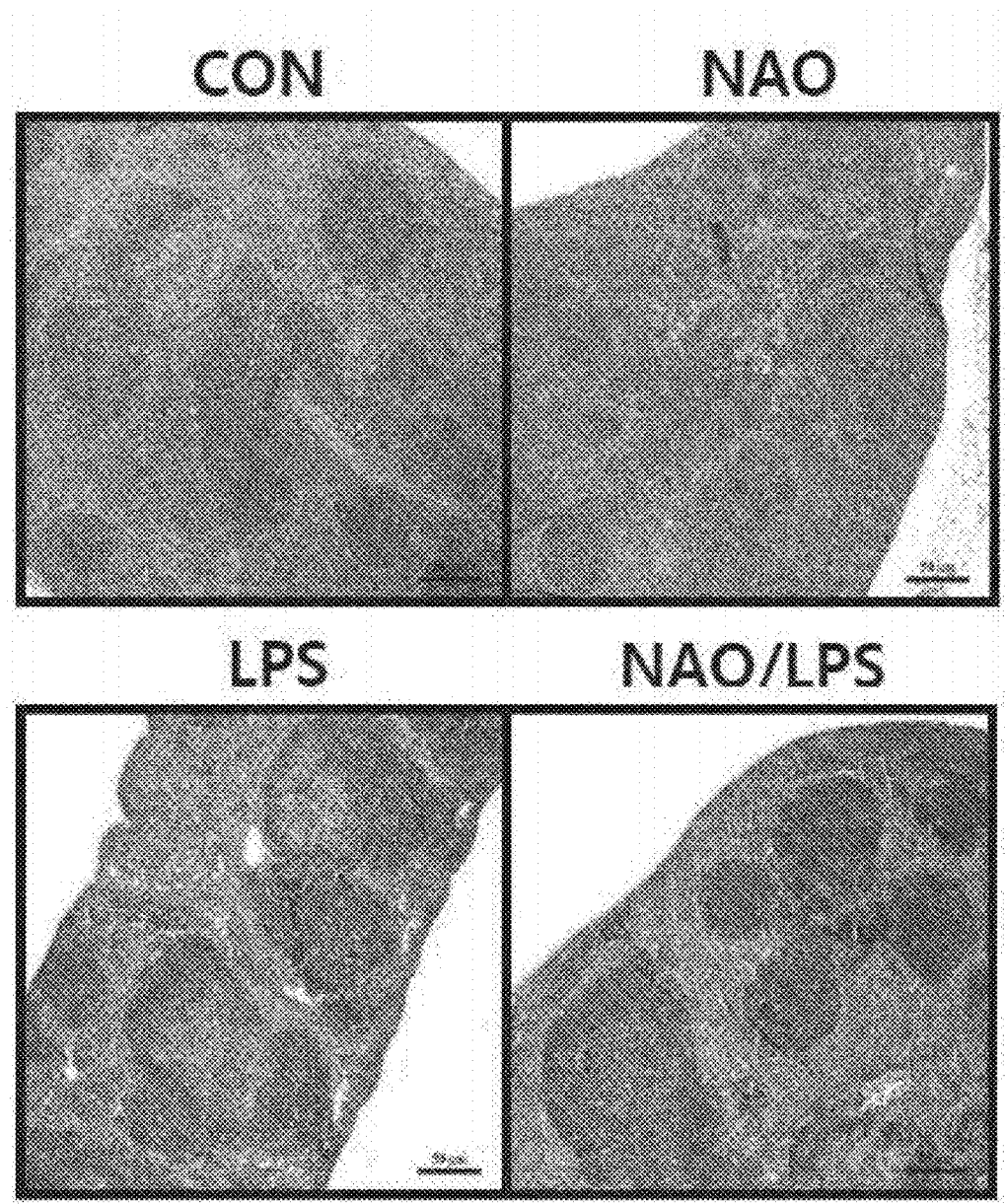
FIG. 11 is a graph showing the degree of apoptosis in the splenic tissue of animal models in which neoagarooligosaccharide of the present invention is pre-treated and LPS is administered.

Further, as shown in FIG. 11, cell death in the spleen tissue, in which the neoagarooligosaccharide was pretreated was significantly inhibited compared to that of the control group.

Through the experimental results, it was confirmed that the neoagarooligosaccharide has excellent effects of preventing sepsis and septic shock and reinforcing immunization by effectively suppressing the expression of inflammation.

Hereinafter, formulation examples of the pharmaceutical composition and the food composition of the present invention will be described, but the present invention is not limited thereto, but is specifically described.

Formulation Example 1: Preparation of Pharmaceutical Composition 1-1. Preparation of Powder
20 mg of neoagarooligosaccharide
100 mg of lactose
10 mg of talc
The components were mixed and packed in an airtight bag so as to prepare powders.

1-2. Preparation of Tablet
10 mg of neoagarooligosaccharide
100 mg of corn starch
100 mg of lactose
2 mg of magnesium stearate The components were mixed and tableted according to a conventional method of preparing tablets so as to prepare tablets.

1-3. Preparation of Capsule 10 mg of neoagarooligosaccharide 3 mg of crystalline cellulose 14.8 mg of lactose 0.2 mg of magnesium stearate The components were mixed and filled in gelatin capsules according to a conventional method of preparing capsules so as to prepare capsules.

1-4. Preparation of Injection 10 mg of neoagarooligosaccharide 180 mg of Mannitol 2974 mg of sterilized water for injection 26 mg of $Na_2HPO_4.2H_2O$ According to a conventional method of preparing injections, 2 ml per ample was prepared as an amount of the components.

1-5. Preparation of Liquid Agent 10 mg of neoagarooligosaccharide 10 g of isomerized glucose 5 g of mannitol appropriate amount of purified water According to a conventional method of preparing liquid agents, each component was added and dissolved in the purified water, and the lemon flavor was added in an appropriate amount. Then, the components were mixed, and then the purified water was added thereto. The whole mixture was then adjusted to 100 ml by adding the purified water and was filled in a brown bottle. Then the mixture was sterilized to prepare liquid agents.

Formulation Example 2: Preparation of Food Composition 2-1. Preparation of Health Food 100 mg of neoagarooligosaccharide appropriate amount of vitamin mixture 70 g of vitamin A acetate 1.0 mg of vitamin E 0.13 mg of vitamin B1

0.15 mg of vitamin B2

0.5 mg of vitamin B6

0.2 g of vitamin B12

10 mg of vitamin C 10 g of biotin 1.7 mg of nicotinic acid amide 50 g of Folic acid 0.5 mg of calcium pantothenate appropriate amount of inorganic mixture 1.75 mg of ferrous sulfate 0.82 mg of zinc oxide 25.3 mg of magnesium carbonate 15 mg of potassium phosphate monobasic 55 mg of potassium phosphate dibasic 90 mg of potassium citrate 100 mg of calcium carbonate 24.8 mg of magnesium chloride Although the composition ratio of the vitamin and mineral mixture is configured to be mixed with comparatively suitable ingredients for health food, the composition ratio may be arbitrarily modified. After the components were mixed according to conventional methods of preparing health foods, granules were prepared and used in the preparation of a health food composition according to conventional methods.

The invention claimed is:

1. A method for treating sepsis or septic shock in a subject, the method comprising administering to the subject a neoagarooligosaccharide, wherein the neoagarooligosaccharide is prepared from agar or agarose by an agarase gene (DagA) enzyme reaction wherein the DagA enzyme is obtained from *Streptomyces coelicolor*.

2. The method of claim 1, wherein the DagA enzyme is obtained from *Streptomyces coelicolor* and has the amino acid residues 31-309 of the amino acid sequence of SEQ ID NO: 2.

3. The method of claim 2, wherein the DagA enzyme is encoded by a nucleotide sequence of SEQ ID NO: 1.

4. The method of claim 1, wherein the neoagarooligosaccharide is selected from the group consisting of neoagarobiose, neoagarotetraose, neoagarohexaose, and any combination thereof.

5. The method of claim 1, wherein the neoagarooligosaccharide is administered at about 0.001 mg/kg to about 1000 mg/kg per day.

6. The method of claim 1, wherein the neoagarooligosaccharide is administered orally, rectally, intravenously, intramuscularly, subcutaneously, or intracerebrally.

7. The method of claim 1, wherein the neoagarooligosaccharide is administered in the form of an injection.

* * * * *

SEQUENCE LISTING

```
<160> NUMBER OF SEQ ID NOS: 4

<210> SEQ ID NO 1
<211> LENGTH: 930
<212> TYPE: DNA
<213> ORGANISM: Streptomyces coelicolor

<400> SEQUENCE: 1
gtggtcaacc gacgtgatct catcaagtgg agtgccgtcg cactcggagc gggtgcgggg      60
ctcgcgggtc ccgcacccgc cgctcatgcc gcagacctcg aatgggaaca gtacccgtg     120 ccggccgccc ctggcggaaa caggtcctgg cagcttctcc ccagccattc ggacgacttc    180
aactacaccg gcaagcctca aaccttcagg ggcagatggc tggaccagca caaggatggc    240
tggtcgggcc cggccaacag cctctacagt gcgcgccatt cctgggtggc tgacggaaat    300
ctcatcgtcg agggccgcag ggcgccggac gggagggtct actgcggcta cgtgacctcc    360 cgcacccag tcgagtaccc tctctatacc gaagtactca tgcgtgtgag cgggctgaag    420
ctctcatcga atttctggct cctgagcaga gacgacgtca acgagattga cgtgatcgaa    480
tgctacggca acgagtcatt gcacggaaag cacatgaaca ccgcctacca catattccag    540
cggaacccct tcactgaact ggcgagaagc cagaaggggt atttcgcaga tgggagctac    600
gggtacaatg gtgagactgg gcaggtgttt ggggacggcg ccgggcaacc tcttcttcgg    660
aatggattcc accgctacgg cgtgcactgg ataagcgcca ccgaattcga tttctacttc    720
aacggcaggt tggtgcgccg gctgaaccgg tcgaacgacc tcagggaccc ccggagccgg    780
```

```
ttcttcgacc agccaatgca tctgatcctc aacaccgaga gtcatcagtg gcgcgtcgac     840
cgaggtatcg aacccacgga cgcggaactc gcagaccca gcatcaacaa catctactac      900
cgctgggtca ggacgtatca ggccgtgtag                                      930
```

<210> SEQ ID NO 2
<211> LENGTH: 309
<212> TYPE: PRT
<213> ORGANISM: Streptomyces coelicolor

<400> SEQUENCE: 2

```
Met Val Asn Arg Arg Asp Leu Ile Lys Trp Ser Ala Val Ala Leu Gly
 1               5                  10                  15

Ala Gly Ala Gly Leu Ala Gly Pro Ala Pro Ala His Ala Ala Asp
             20                  25                  30

Leu Glu Trp Glu Gln Tyr Pro Val Pro Ala Pro Gly Gly Asn Arg
         35                  40                  45

Ser Trp Gln Leu Leu Pro Ser His Ser Asp Asp Phe Asn Tyr Thr Gly
     50                  55                  60

Lys Pro Gln Thr Phe Arg Gly Arg Trp Leu Asp Gln His Lys Asp Gly
 65                  70                  75                  80

Trp Ser Gly Pro Ala Asn Ser Leu Tyr Ser Arg His Ser Trp Val
                 85                  90                  95

Ala Asp Gly Asn Leu Ile Val Glu Gly Arg Arg Ala Pro Asp Gly Arg
                100                 105                 110

Val Tyr Cys Gly Tyr Val Thr Ser Arg Thr Pro Val Glu Tyr Pro Leu
            115                 120                 125

Tyr Thr Glu Val Leu Met Arg Val Ser Gly Leu Lys Leu Ser Ser Asn
        130                 135                 140

Phe Trp Leu Leu Ser Arg Asp Asp Val Asn Glu Ile Asp Val Ile Glu
145                 150                 155                 160

Cys Tyr Gly Asn Glu Ser Leu His Gly Lys His Met Asn Thr Ala Tyr
                165                 170                 175

His Ile Phe Gln Arg Asn Pro Phe Thr Glu Leu Ala Arg Ser Gln Lys
            180                 185                 190

Gly Tyr Phe Ala Asp Gly Ser Tyr Gly Tyr Asn Gly Glu Thr Gly Gln
        195                 200                 205

Val Phe Gly Asp Gly Ala Gly Gln Pro Leu Leu Arg Asn Gly Phe His
    210                 215                 220

Arg Tyr Gly Val His Trp Ile Ser Ala Thr Glu Phe Asp Phe Tyr Phe
225                 230                 235                 240

Asn Gly Arg Leu Val Arg Arg Leu Asn Arg Ser Asn Asp Leu Arg Asp
                245                 250                 255

Pro Arg Ser Arg Phe Phe Asp Gln Pro Met His Leu Ile Leu Asn Thr
            260                 265                 270

Glu Ser His Gln Trp Arg Val Asp Arg Gly Ile Glu Pro Thr Asp Ala
        275                 280                 285

Glu Leu Ala Asp Pro Ser Ile Asn Asn Ile Tyr Tyr Arg Trp Val Arg
    290                 295                 300

Thr Tyr Gln Ala Val
305
```

<210> SEQ ID NO 3
<211> LENGTH: 27
<212> TYPE: DNA

-continued

```
<213> ORGANISM: Artificial Sequence
<220> FEATURE:
<223> OTHER INFORMATION: Description of Artificial Sequence: Synthetic
      forward primer(Asm-F)

<400> SEQUENCE: 3
gacatatggt ggtcaaccga cgtgatc                                          27

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      reverse primer(Asm-R)

<400> SEQUENCE: 4
ggtggatccc tacacggcct gatacg                                           26
```